United States Patent
Kim et al.

(10) Patent No.: US 8,504,148 B2
(45) Date of Patent: Aug. 6, 2013

(54) NEURAL DEVICE HAVING VIA-HOLE CONNECTION AND USING AT LEAST ONE NANO-WIRE

(75) Inventors: Donghyun Kim, Seoul (KR); Jongill Hong, Seoul (KR); Gunhee Han, Gyeonggi-do (KR); Taewook Kim, Seoul (KR); Heonjin Choi, Seoul (KR); Seunghan Park, Seoul (KR); Seongyeol Pyo, Daejeon (KR); Sooho Bae, Daejeon (KR); Han Chung, Daejeon (KR)

(73) Assignees: Industry-Academic Cooperation Foundation, Yonsei University, Seoul (KR); I3SYSTEM, Inc., Daejeon (KR)

( * ) Notice: Subject to any disclaimer, the term of this patent is extended or adjusted under 35 U.S.C. 154(b) by 271 days.

(21) Appl. No.: 13/055,670

(22) PCT Filed: Oct. 8, 2010

(86) PCT No.: PCT/KR2010/006903
§ 371 (c)(1),
(2), (4) Date: Jan. 24, 2011

(87) PCT Pub. No.: WO2011/142509
PCT Pub. Date: Nov. 17, 2011

(65) Prior Publication Data
US 2012/0130459 A1    May 24, 2012

(30) Foreign Application Priority Data
May 11, 2010  (KR) .................. 10-2010-0044044

(51) Int. Cl.
*A61N 1/375*    (2006.01)

(52) U.S. Cl.
USPC .................................................. 607/2

(58) Field of Classification Search
USPC ............................................ 607/2, 148
See application file for complete search history.

(56) References Cited

U.S. PATENT DOCUMENTS

| | | | |
|---|---|---|---|
| 8,195,266 B2 * | 6/2012 | Whalen et al. ............ | 600/373 |
| 2004/0133118 A1 | 7/2004 | Llinas | |
| 2007/0187238 A1 | 8/2007 | Whalen, III et al. | |
| 2010/0106259 A1 | 4/2010 | Llinas et al. | |

FOREIGN PATENT DOCUMENTS
KR    10 2009 0041309 A    4/2009

OTHER PUBLICATIONS

ISA Korean Intellectual Property Office, International Search Report of PCT/KR2010/006903, Jun. 30, 2011, 7 pages.
Ishida, M. et al., "Silicon Smart Microchips for Intelligent Sensing," Symposium on VLSI Technology Digest of Technical Papers, pp. 6-9, 2008, 4 pages.

* cited by examiner

*Primary Examiner* — Scott Getzow
*Assistant Examiner* — Amanda Patton
(74) *Attorney, Agent, or Firm* — Alleman Hall McCoy Russell & Tuttle LLP

(57) ABSTRACT

Provided is a neural device including at least one nano-wire. The neural device includes a nano-wire formed on a base formed on a first surface of a substrate, and an electrode pad formed on a second surface different from the first surface of the substrate and configured to output an electrical signal gained from a neural fiber through the nano-wire or apply a signal for an electric stimulus to the nano-wire. Therefore, it is possible to prevent the nano-wire from becoming embedded in an encapsulation and maximize a contact between the nano-wire and a nerve.

10 Claims, 7 Drawing Sheets cluster formation    nucleation and growth    nanowire

NEURAL DEVICE HAVING VIA-HOLE CONNECTION AND USING AT LEAST ONE NANO-WIRE

TECHNICAL FIELD

The present invention relates to a neural device having a wire configured to transmit and receive an electrical signal, and more particularly, to a structure of a neural device having a wire capable of effectively gaining an electrical signal generated from a nerve and applying an electrical stimulus to the nerve.

BACKGROUND ART

In general, muscles of a human body are operated according to electrical stimuli provided from nerves. Accordingly, when abnormality of facial muscles occurs, treatment of nerves connected to the corresponding muscles may be needed.

When abnormality of facial nerves or laryngeal nerves occurs, treatments such as drugs, surgery, etc. are performed. In this case, patients receive local massages of corresponding parts in order to stimulate peripheral nerves during recovery of damaged nerves, preventing atrophy of the muscles.

That is, when stimuli to the muscles are obstructed due to surgery, etc. of facial or laryngeal nerve paralytics, since the corresponding muscles may be damaged, causing permanent muscle damage or paralysis, methods of massaging muscles related to the corresponding nerve system or providing electrical stimuli from the outside, etc. have been proposed.

For this, a device configured to be inserted into a human body to provide a physical stimulus or gain information of a certain numerical value in the human body has been proposed, and in particular, a technique of invasively measuring a neural signal in vivo using a nano-wire has been introduced.

A probe configured to measure a neural signal may be connected to a gate or a drain of a complementary metal-oxide semiconductor (CMOS), but each conventional neural device has a probe and an electrode pad configured to input/output a neural signal detected by the probe and power of the neural device, which are formed on the same surface.

In this case, there is no problem when a neural cell is cultivated on a device or a length of the probe is substantially larger than a height of an encapsulation of an electrode pad such that the probe can be substantially inserted into the nerve. However, since a length of the nano-wire to be formed is basically limited to about 100 µm, when the probe is disposed on the same surface as the encapsulation of the electrode pad having a thickness larger than the length of the nano-wire, the probe cannot be inserted to the nerve to a substantial depth.

FIG. 1 is a drawing showing a conventional neural device.

Referring to FIG. 1, the conventional neural device includes a nano-wire 110 connected to a CMOS 140, an electrode pad 120, and an encapsulation 130.

As shown in FIG. 1, the nano-wire 110 and the electrode pad 120 configured to input/output a neural signal detected by the nano-wire 110 and power of the device are formed on the same surface.

Therefore, the nano-wire 110 cannot be deeply inserted into the nerve due to disturbance of the encapsulation 130, and thus, vital signal measurement using the nano-wire may encounter a serious obstruction.

DISCLOSURE

Technical Problem

In order to solve the foregoing and/or other problems, it is an object of the present invention to provide a neural device having a nano-wire that cannot be easily manufactured to a certain length or more, configured such that insertion of the nano-wire into a nerve is not disturbed by an encapsulation of an electrode pad.

In addition, it is another object of the present invention to provide a neural device in which a formation direction of a nano-wire is differently set from a direction of an electrode pad for electrical connection such that insertion of the nano-wire into a nerve is not disturbed.

Further, it is still another object of the present invention to provide a neural device in which a nano-wire probe is guided to a rear surface of a substrate using a through via-hole to prevent the nano-wire probe from being embedded by an encapsulation and to maximize contact between the nano-wire probe and a nerve.

Furthermore, it is yet another object of the present invention to provide a neural device capable of removing a conductive wire connection needed for encapsulation and connecting a nano-wire probe end to the device or an external wire of the device using a touch ball, minimizing a thickness of the device.

Technical Solution

One aspect of the present invention provides a neural device including: a nano-wire formed on a base formed on a first surface of a substrate; and an electrode pad formed on a second surface different from the first surface of the substrate and configured to output an electrical signal gained from a neural fiber through the nano-wire or apply a signal for an electric stimulus to the nano-wire.

In this case, the second surface may be a surface having an angle of 170° to 180° between a normal vector of the second surface and a normal vector of the first surface, and the nano-wire and the electrode pad may be connected to each other through a through via-hole.

In this case, the electrode pad may be connected to the outside through a touch ball.

In this case, the through via-hole may be disposed out of a CMOS region of the substrate.

In this case, the base may include a through-hole connected to the through via-hole and a nano-wire support frame configured to support the nano-wire.

In this case, the nano-wire may be formed by a catalyst disposed on the nano-wire support frame through a lithography process and a reactant supplied through a chemical vapor deposition (CVD) process and reacting with the catalyst.

In this case, the nano-wire may be formed by physically or chemically etching a periphery of the nano-wire.

Another aspect of the present invention provides a nano-wire probe device including: a touch ball electrically connected to an electrode pad to be connected to a device; and a nano-wire formed on a base formed in a direction opposite to the electrode pad, and configured to provide an electrical signal measured from a neural fiber to the device through the touch ball or apply an electrical stimulus on the basis of a signal applied from the device through the touch ball.

In this case, the base may include a through-hole connected to the through via-hole and a nano-wire support frame configured to support the nano-wire.

Advantageous Effects

According to the present invention, when a nano-wire that cannot be easily manufactured to a certain length or more is inserted into a nerve, the insertion can be undisturbed by an encapsulation of an electrode pad.

In addition, a formation direction of a nano-wire is differently set from a direction of an electrode pad for electrical connection such that insertion of the nano-wire into a nerve can be undisturbed.

Further, a nano-wire probe is guided to a rear surface of a substrate using a through via-hole to prevent the nano-wire probe from being embedded by an encapsulation and to maximize contact the nano-wire probe with a nerve.

Furthermore, a conductive wire connection needed for encapsulation is removed and a nano-wire probe end is connected to a device or an external wire of the device using a touch ball, minimizing a thickness of the device.

DESCRIPTION OF DRAWINGS

The above and other objects, features and advantages of the present invention will be more apparent from the following detailed description taken in conjunction with the accompanying drawings, in which.

MODES FOR INVENTION

Figure 1:
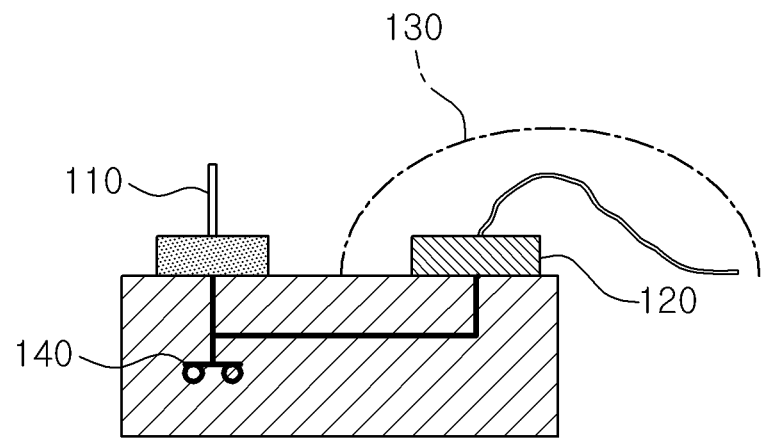
FIG. 1 is a drawing showing a conventional neural device.

Exemplary embodiments of the present invention will now be described in detail with reference to the accompanying drawings. In this case, to clearly describe the present invention, repeated descriptions and detailed description of already known functions and components, which may obscure the sprit of the present invention, will be omitted. The following embodiments are described in order to enable those of ordinary skill in the art to embody and practice the present invention. Accordingly, shapes and sizes of elements in the drawings may be exaggerated for the purpose of clarity.

Hereinafter, exemplary embodiments in accordance with the present invention will be described in detail with reference to the accompanying drawings.

Figure 2:
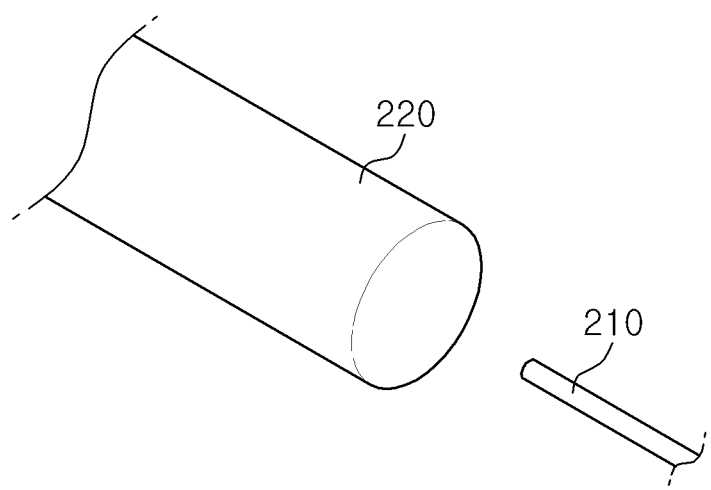
FIG. 2 is a drawing showing an example of a nano-wire included in a neural device in accordance with an exemplary embodiment of the present invention.

FIG. 2 is a drawing showing an example of a nano-wire included in a neural device in accordance with an exemplary embodiment of the present invention.

Referring to FIG. 2, a nano-wire 210 is inserted into a neural fiber 220 or a neural tissue to gain an electrical signal or provide an electrical stimulus.

That is, the nano-wire 210 according to the embodiment is inserted into the neural fiber 220 in a nerve bundle to gain an electrical signal generated along a surface of the neural fiber 220 or provide an electrical stimulus to the neural fiber 220.

Anatomically, a nerve is a thin and long structure that can be observed with the naked eye, and histologically, is a collection of a great number of nerve bundles. Meanwhile, the nerve bundle is a collection of a great number of nerve fibers. The nerve fiber is an axon part of a neural cell, and is called a nerve fiber because the axon has a thin and long shape like a fiber. The nerve fiber may be called by various names such as a neurite/axon, etc.

Each nerve fiber is surrounded by an endoneurium, the nerve bundle is surrounded by a perineurium, and the nerve that is a collection of nerve bundles is surrounded by an epineurium, all of which are soft connective tissues and exist to protect the nerve. In this case, only the epineurium is distinguishable with the naked eye.

The nano-wire 210 has a diameter of tens to hundreds of nm and can be inserted into a portion of the neural fiber 220. In general, since the neural fiber 220 has a diameter of several μm, even when the nano-wire 210 is inserted into the neural fiber 220, damage to the neural fiber is small.

Since the nano-wire 210 is used to gain an electrical signal and provide an electrical stimulus, damage to the neural fiber can be minimized.

As shown in FIG. 2, the nano-wire may be inserted in a longitudinal direction of the neural fiber. When the nano-wire is inserted in the longitudinal direction, a contact area between the nano-wire and an outer part of the neural fiber can be easily maximized.

Figure 3:
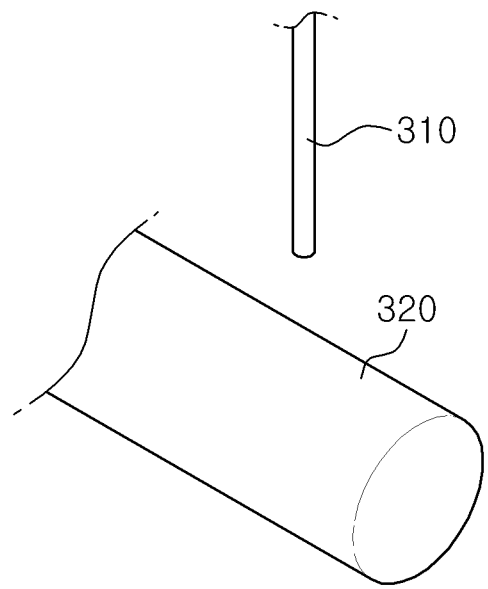
FIG. 3 is a drawing showing another example of the nano-wire included in a neural device in accordance with an exemplary embodiment of the present invention.

In this case, an insertion direction of the nano-wire is not limited thereto, but a nano-wire 310 may be inserted in a direction perpendicular to the neural fiber 320, as shown in FIG. 3.

FIG. 3 is a drawing showing another example of the nano-wire included in a neural device in accordance with an exemplary embodiment of the present invention.

Referring to FIG. 3, it can be seen that the nano-wire 310 is inserted in the direction perpendicular to the neural fiber 320.

The neural device in accordance with the present invention may include an electrode pad and a process module, in addition to the nano-wire.

The electrode pad may be installed to be connected to the process module configured to process an electrical signal detected from the neural fiber. The process module controls an operation of gaining an electrical signal from the neural fiber or applying an electrical signal to the neural fiber. In particular, according to the present invention, the electrode pad connected to the process module may be formed at a different surface from a surface on which the nano-wire is formed.

That is, since the surface on which the nano-wire is formed is different from the surface on which the electrode is formed, when the nano-wire is inserted into a nerve, the nano-wire can be deeply inserted into the skin without interruption by the electrode.

Figure 4:
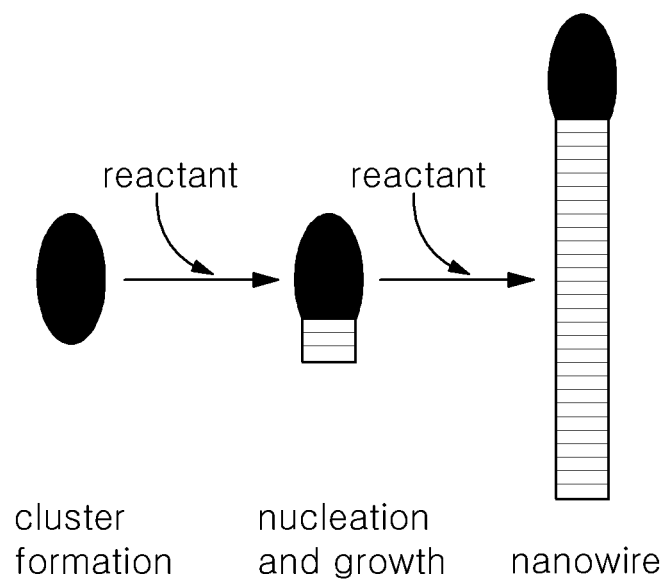
FIG. 4 is a conceptual drawing showing a method of synthesizing a nano-wire using a catalyst.

FIG. 4 is a conceptual drawing showing a method of synthesizing a nano-wire using a catalyst.

Referring to FIG. 4, when a reactant is applied to a nano cluster, a nano-wire is synthesized by nucleation and growth.

Figure 5:
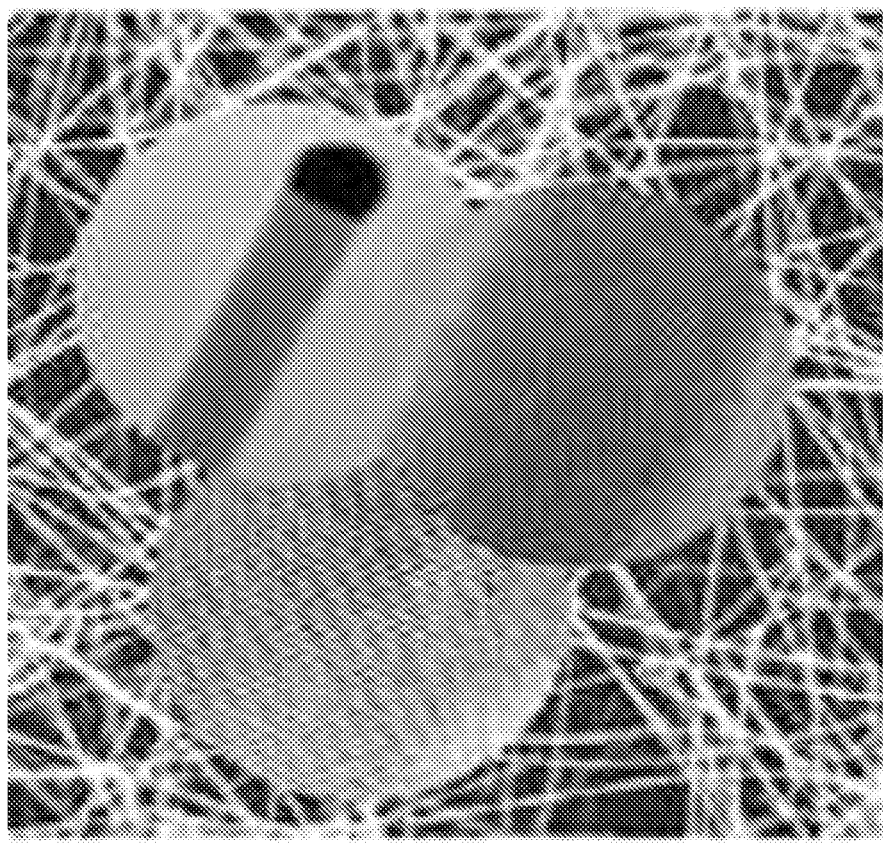
FIG. 5 is a drawing showing a shape of the synthesized nano-wire.

The synthesized nano-wire may have a shape shown in FIG. 5. In addition, the nano-wire used in the embodiment may also be formed by a method described in Korean Patent Laid-open Publication No. 2009-0041309, etc.

FIG. 5 is a drawing showing a shape of the synthesized nano-wire.

Figure 6:
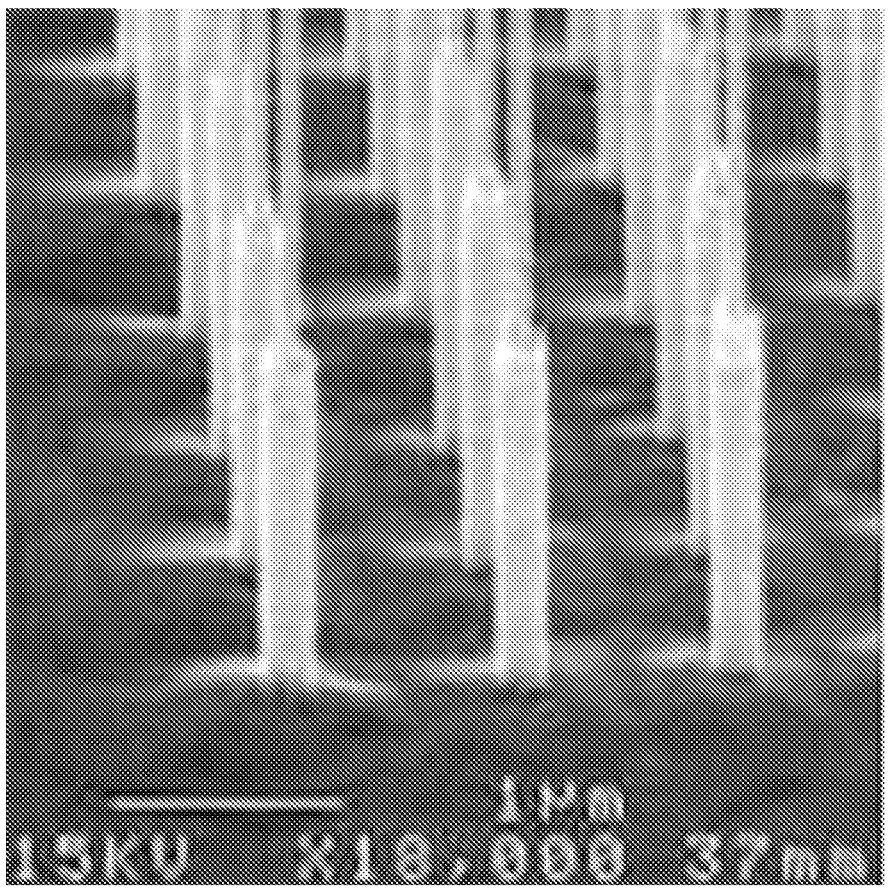
FIG. 6 is a drawing showing a nano-wire arrangement having a three-dimensional structure formed by the above description.

FIG. 6 is a drawing showing a nano-wire arrangement having a three-dimensional structure formed by the above description.

Figure 7:
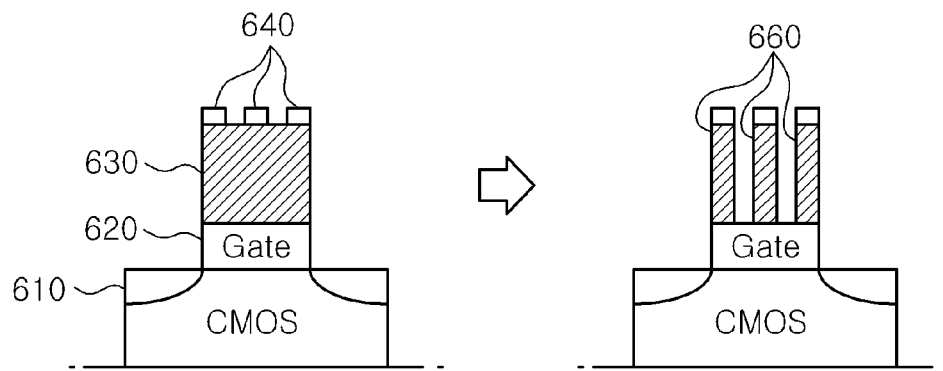
FIG. 7 is a conceptual drawing showing a method of forming a nano-wire by etching.

FIG. 7 is a conceptual drawing showing a method of forming a nano-wire by etching.

Referring to FIG. 7, it can be seen that an electrode 630 is formed on a gate 620 of a CMOS 610, and a photoresistor 640 for nano-wire etching is formed on the electrode 630.

Next, when an unnecessary portion is removed through physical or chemical etching, only a nano-wire 660 remains intact as shown in FIG. 7.

Figure 8:
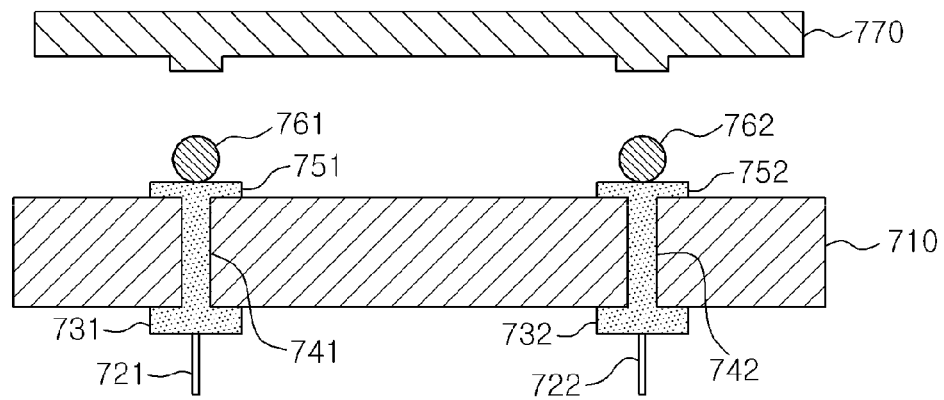
FIG. 8 is a drawing showing a neural device in accordance with an exemplary embodiment of the present invention.

FIG. 8 shows a neural device in accordance with an exemplary embodiment of the present invention.

Referring to FIG. 8, the neural device in accordance with an exemplary embodiment of the present invention includes a substrate 710, nano-wires 721 and 722, electrodes 731 and 732, through via-holes 741 and 742, electrode pads 751 and 752, and touch balls 761 and 762.

The electrodes 731 and 732 of the nano-wires 721 and 722 are connected to the electrode pads 751 and 752 disposed at an opposite surface of the substrate through the through via-holes 741 and 742, respectively. That is, the electrode 731 of the nano-wire 721 is connected to the electrode pad 751 through the through via-hole 741, and the electrode 732 of the nano-wire 722 is connected to the electrode pad 752 through the through via-hole 742.

That is, the nano-wire and the electrode pad disposed at opposite surfaces of the substrate are connected to each other using a through via-hole technique. Since the surface of the substrate on which the nano-wire is installed is opposite to the surface of the substrate on which the electrode pad is installed, an angle between normal vectors thereof is about 180°.

The electrode pad 751 outputs an electrical signal gained from the neural fiber through the nano-wire 721 or applies a signal for an electrical stimulus to the nano-wire 721. The electrode pad 752 outputs an electrical signal gained from the neural fiber through the nano-wire 722 or applies a signal for an electrical stimulus to the nano-wire 722.

The electrode pad 751 is connected to the outside through the touch ball 761, and the electrode pad 752 is connected to the outside through the touch ball 762. Reference numeral 770 shown in FIG. 8 represents an electrode pad connected to the outside. According to an embodiment, reference numeral 770 may be a process module configured to control an operation of gaining an electrical signal from the neural fiber or applying an electrical to the neural fiber.

While not shown in FIG. 8, a CMOS region may be provided on the substrate. The CMOS region is a region on the substrate used to implement a CMOS. The through via-holes 741 and 742 may be disposed out of the CMOS region.

While not shown in FIG. 8, bases may be installed at the electrodes 731 and 732 to position the nano-wires, respectively.

Each of the bases may have at least one through-hole. The through-hole may have various cross-sections such as a circular shape, an oval shape, a polygonal shape, etc., and in particular, a circular shape, which can be easily manufactured, or a shape corresponding to a cross-section of a nerve bundle. In this case, the through-hole may have a diameter of tens of μm to tens of nm.

In particular, the through-hole formed in the base may be connected to a through via-hole formed in the substrate. In this case, the neural fiber may be recovered through the through-hole or the through via-hole.

In addition, the base may be provided with a nano-wire support frame configured to support the nano-wire. In this case, the nano-wire support frame may be installed at an inner circumference of the through-hole. The nano-wire support frame supports the nano-wire so that the nano-wire can be fixed in one direction. That is, the nano-wire is fixed by the nano-wire support frame.

The nano-wire support frame may be configured to divide the through-hole into a plurality of regions. The nano-wire support frame may have a straight shape or a curved shape having various radii of curvature. In addition, the nano-wire support frame may extend from the inner circumference of the through-hole or extend from one surface of the base.

The base including the through-hole and the nano-wire support frame may be formed on a wafer formed of various materials such as silicon, etc. through a photo mask and etching process.

When the base including the through-hole and the nano-wire support frame is formed, a catalyst is positioned at a position at which the nano-wire on the nano-wire support frame grows. For example, when the nano-wire is fixed to a middle portion of the nano-wire support frame, the catalyst is positioned at the middle portion of the nano-wire support frame to grow the nano-wire. The catalyst may be positioned at an arbitrary portion of the nano-wire support frame through a lithography process, etc. The catalyst may be selected according to a material of the nano-wire to be grown. For example, when a silicon nano-wire grows, an Au catalyst may be used. When the catalyst is positioned on the substrate, a reactant may be supplied process to complete the nano-wire through a chemical vapor deposition (CVD).

The base, the nano-wire support frame and the nano-wire may be formed of various materials. For example, the nano-wire support frame and the nano-wire may be an electrode appropriate to a living body such as silicon, gold, silver (Ag), ruthenium (Ru), titanium nitride (TiN) and copper, or a semiconductor device or a metal, which may be implemented as a nano device by a nano process.

Figure 9:
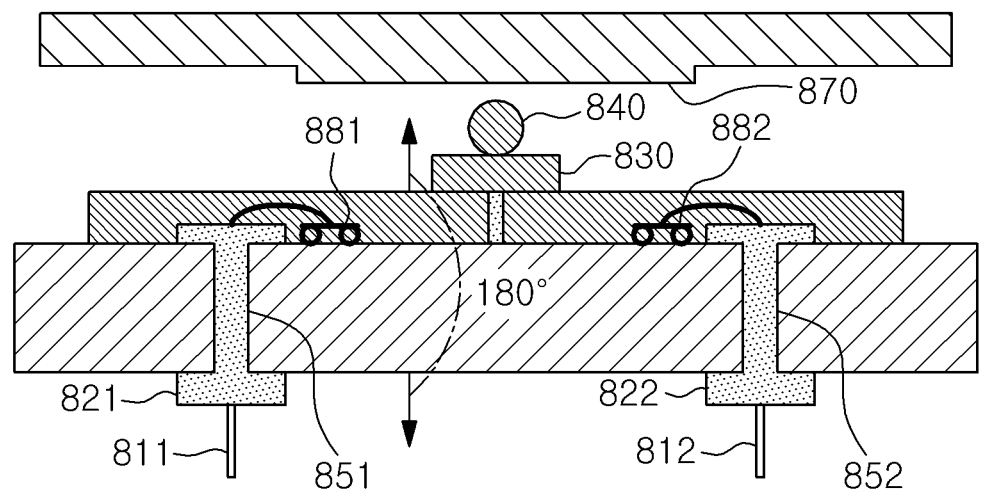
FIG. 9 is a drawing showing a neural device in accordance with another exemplary embodiment of the present invention.

FIG. 9 is a drawing showing a neural device in accordance with another exemplary embodiment of the present invention.

While FIG. 9 is similar to FIG. 8, it is emphasized that a nano-wire probe is connected to a gate or a drain of a CMOS.

Referring to FIG. 9, the neural device in accordance with an exemplary embodiment of the present invention includes nano-wires 811 and 812, electrodes 821 and 822, through via-holes 851 and 852, CMOSs 881 and 882, an electrode pad 830 and a touch ball 840.

While the electrode pad 830 and the touch ball 840 are, for example, singly shown in an example shown in FIG. 9, at least two electrode pads and at least two touch balls may be provided according to the number of nano-wires 811 and 812.

The electrodes 821 and 822 of the nano-wires 811 and 812 are connected to an opposite surface of a substrate through the through via-holes 851 and 852. In this case, the nano-wires 811 and 812 are connected to drains or gates of the CMOSs 881 and 882, respectively.

The electrode pad 830 outputs an electrical signal gained from a neural fiber through the nano-wire 811 or 812, or applies a signal for an electrical stimulus to the nano-wire 811 or 812.

The electrode pad 830 is connected to the outside through the touch ball 840. Reference numeral 870 shown in FIG. 9 represents an electrode pad connected to the outside. According to an embodiment, reference numeral 870 may be a process module configured to control an operation of gaining an electrical signal from a neural fiber or applying an electrical signal to the neural fiber.

Figure 10:
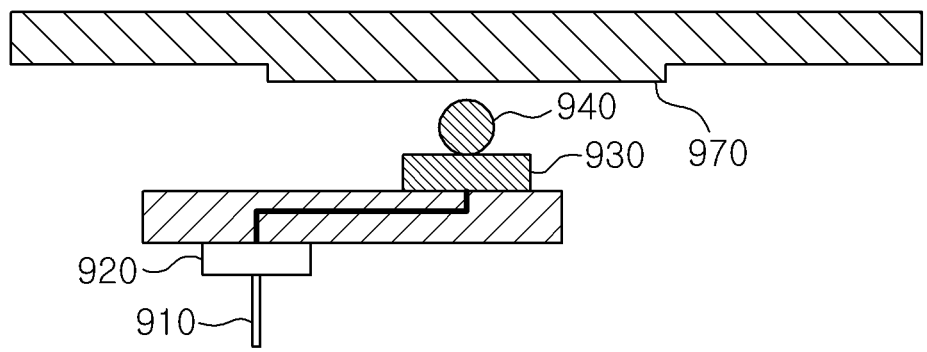
FIG. 10 is a drawing showing a nano-wire probe device in accordance with an exemplary embodiment of the present invention.

FIG. 10 is a drawing showing a nano-wire probe device in accordance with an exemplary embodiment of the present invention.

Referring to FIG. 10, the nano-wire probe device in accordance with an exemplary embodiment of the present invention includes a nano-wire 910, an electrode 920, an electrode pad 930 and a touch ball 940.

The touch ball 940 is electrically connected to an electrode pad connected to a device (i.e., an external electrode pad).

The nano-wire 910 is formed at a surface of a base opposite to the touch ball 940, and provides an electrical signal measured from a neural fiber to the device through the touch ball 940 or applies an electrical stimulus from the device to the neural fiber on the basis of a signal applied through the touch ball 940.

The nano-wire 910 is connected to the touch ball 940 through the electrode 920 and the electrode pad 930.

The embodiment shown in FIG. 10 corresponds to a case in which only the nano-wire probe device in contact with the substrate through the touch ball 940 is separated. That is, the embodiment shown in FIG. 10 shows a method of connecting a nano-wire probe end made using a through via-hole, independently from the device, to the device using the touch ball. The technical sprit of the present invention includes both of a case in which the nano-wire and a contact pad are connected to each other using the through via-hole of the substrate (included in a device), and a case in which the probe device in which the nano-wire and the contact pad connected to the touch ball are disposed at opposite surfaces is electrically connected to the substrate using the touch ball (independently configured from the device).

Figure 11:
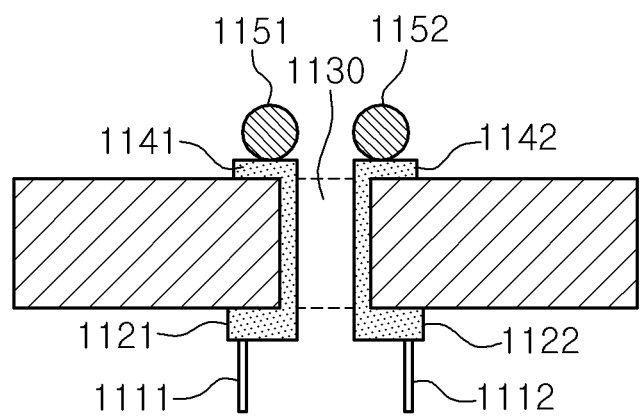
FIG. 11 is a drawing showing another example of connection between an electrode and a pad, which are disposed at opposite surfaces of a substrate, through a through via-hole.

FIG. 11 is a drawing showing another example of connection between an electrode and a pad, which are disposed at opposite surfaces of a substrate, through a through via-hole.

Referring to FIG. 11, electrodes 1121 and 1122, on which nano-wires 1111 and 1112 are formed, are connected to electrode pads 1141 and 1141 through a through via-hole 1130, respectively. That is, the electrode 1121 is connected to the electrode pad 1141, and the electrode 1122 is connected to the electrode pad 1142.

A touch ball 1151 is formed on the electrode pad 1141, and a touch ball 1152 is formed on the electrode pad 1142.

In the example shown in FIG. 11, connection between the electrodes 1121 and 1122 and the electrode pads 1141 and 1142 is performed by a portion of the through via-hole 1130, and the remaining portion of the through via-hole 1130 remains intact as it is. That is, the through via-hole 1130 need not be entirely filled with a metal. Only a partial space may be filled with a metal and the electrodes on both surfaces of a substrate may be connected to each other, and the remaining portion may remain as a space. In this case, an outer surface of the remaining hole portion may be coated.

In this case, a neural fiber, a neural tissue, etc. may grow through the remaining hole portion.

Further, a through-hole formed in a base may be connected to a through via-hole formed in the substrate. In this case, the neural fiber may be recovered through the through-hole or the through via-hole, and a space in the through via-hole may be effectively used to recover the neural fiber or the neural tissue as the space is increased.

As can be seen from the foregoing, the neural device and the nano-wire probe device in accordance with the present invention are not limited to the configuration and method of the embodiments described above, but all or some components of the embodiments may be configured to be selectively combined such that various modifications of the embodiments can be implemented.

While this invention has been described with reference to exemplary embodiments thereof, it will be clear to those of ordinary skill in the art to which the invention pertains that various modifications may be made to the described embodiments without departing from the spirit and scope of the invention as defined in the appended claims and their equivalents.

The invention claimed is:

1. A neural device comprising:
    a nano-wire formed on a base which is formed on a first surface of a substrate; and
    an electrode pad formed on a second surface different from the first surface of the substrate, and configured to output an electrical signal gained from a neural fiber through the nano-wire or apply a signal for an electric stimulus to the nano-wire,
    wherein the second surface is a surface having an angle of 170° to 180° between a normal vector of the second surface and a normal vector of the first surface, and the nano-wire and the electrode pad are connected to each other using a through via-hole, and
    wherein the electrode pad is connected to the outside of the neural device through a touch ball.

2. The neural device according to claim 1, wherein the through via-hole is disposed outside of a CMOS region of the substrate.

3. The neural device according to claim 2, wherein the base comprises a through-hole connected to the through via-hole and a nano-wire support frame configured to support the nano-wire.

4. The neural device according to claim 3, wherein the nano-wire is formed by a catalyst disposed on the nano-wire support frame through a lithography process and a reactant supplied through a chemical vapor deposition (CVD) process and reacting with the catalyst.

5. The neural device according to claim 3, wherein the nano-wire is formed by etching a periphery of the nano-wire.

6. A nano-wire probe device comprising:
    a touch ball electrically connected to an electrode pad to be connected to a device; and
    a nano-wire formed on a base which is formed on a substrate, wherein the electrode pad is on a side of the substrate and the base is on the opposite side of the substrate, and the nano-wire is configured to provide an electrical signal measured from a neural fiber to the device through the touch ball or apply an electrical stimulus on the basis of a signal applied from the device through the touch ball.

7. The nano-wire probe device according to claim 6, wherein the electrode pad and the nano-wire are connected to each other using a through via-hole.

8. The nano-wire probe device according to claim 7, wherein the base comprises a through-hole connected to the through via-hole and a nano-wire support frame configured to support the nano-wire.

9. The nano-wire probe device according to claim 8, wherein the nano-wire is formed by a catalyst disposed on the nano-wire support frame through a lithography process and a reactant supplied through a chemical vapor deposition (CVD) process and reacting with the catalyst.

10. The nano-wire probe device according to claim 8, wherein the nano-wire is formed by etching a periphery of the nano-wire.

\* \* \* \* \*